US011379516B2

(12) United States Patent
Peng et al.

(10) Patent No.: US 11,379,516 B2
(45) Date of Patent: Jul. 5, 2022

(54) SIMILAR MEDICAL IMAGE SEARCH

(71) Applicant: GOOGLE LLC, Monntain View, CA (US)

(72) Inventors: Lily Peng, Mountain View, CA (US); Martin Stumpe, Mountain View, CA (US); Daniel Smilkov, Mountain View, CA (US); Jason Hipp, Mountain View, CA (US)

(73) Assignee: Google LLC, Mountain View, CA (US)

( * ) Notice: Subject to any disclaimer, the term of this patent is extended or adjusted under 35 U.S.C. 154(b) by 10 days.

(21) Appl. No.: 16/978,102

(22) PCT Filed: Mar. 29, 2018

(86) PCT No.: PCT/US2018/025054
§ 371 (c)(1),
(2) Date: Sep. 3, 2020

(87) PCT Pub. No.: WO2019/190518
PCT Pub. Date: Oct. 3, 2019

(65) Prior Publication Data
US 2021/0019342 A1    Jan. 21, 2021

(51) Int. Cl.
*G06F 16/532* (2019.01)
*G06F 16/55* (2019.01)
(Continued)

(52) U.S. Cl.
CPC ...... *G06F 16/532* (2019.01); *G06F 16/24578* (2019.01); *G06F 16/538* (2019.01);
(Continued)

(58) Field of Classification Search
CPC .... G06F 16/532; G06F 16/55; G06F 16/5854; G06F 16/538; G06F 16/24578
(Continued)

(56) References Cited

U.S. PATENT DOCUMENTS 7,027,633 B2   4/2006   Foran et al.
7,188,103 B2   3/2007   Furuhashi et al.
(Continued)

FOREIGN PATENT DOCUMENTS

JP   2007 275408   10/2007
JP   2017 099907   6/2017
WO   2018/156133   2/2017

OTHER PUBLICATIONS

J. Wang, et al., Learning fine-grained image similarity with deep ranking, https://arxiv.org/abs/1404.4661 (2017).
(Continued)

*Primary Examiner* — Kimberly L Wilson
(74) *Attorney, Agent, or Firm* — McDonnell Boehnen Hulbert & Berghoff LLP

(57) ABSTRACT

A system for searching for similar medical images includes a reference library in the form of a multitude of medical images, at least some of which are associated with metadata including clinical information relating to the specimen or patient associated with the medical images. A computer system is configured as a search tool for receiving an input image query from a user. The computer system is trained to find one or more similar medical images in the reference library system which are similar to the input image. The reference library is represented as an embedding of each of the medical images projected in a feature space having a plurality of axes, wherein the embedding is characterized by two aspects of a similarity ranking: (1) visual similarity, and (2) semantic similarity such that neighboring images in the feature space are visually similar and semantic information is represented by the axes of the feature space. The computer system supports additional queries from a user to thereby further refine a search for medical images similar to the input
(Continued)

image within a search space consisting of the one or more similar medical images.

20 Claims, 15 Drawing Sheets

(51) Int. Cl.
    *G06F 16/583*    (2019.01)
    *G06F 16/538*    (2019.01)
    *G06F 16/2457*   (2019.01)
    *G16H 30/20*     (2018.01)
    *G16H 50/20*     (2018.01)
    *G06K 9/62*      (2022.01)
    *G06V 10/75*     (2022.01)

(52) U.S. Cl.
    CPC .......... *G06F 16/55* (2019.01); *G06F 16/5854* (2019.01); *G06K 9/6215* (2013.01); *G16H 30/20* (2018.01); *G16H 50/20* (2018.01); *G06V 10/759* (2022.01); *G06V 2201/03* (2022.01)

(58) Field of Classification Search
    USPC ........................................................ 707/723
    See application file for complete search history.

(56) References Cited

U.S. PATENT DOCUMENTS

| | | | |
|---|---|---|---|
| 8,060,178 B2* | 11/2011 | Zhou | G06K 9/6276 600/407 |
| 8,199,994 B2 | 6/2012 | Amir | |
| 9,081,822 B2 | 7/2015 | Xu et al. | |
| 9,275,456 B2 | 3/2016 | Mori et al. | |
| 9,715,642 B2 | 7/2017 | Szegedy et al. | |
| 10,460,211 B2 | 10/2019 | Vanhoucke et al. | |
| 2003/0013951 A1 | 1/2003 | Stefanescu et al. | |
| 2007/0258630 A1 | 11/2007 | Tobin et al. | |
| 2010/0017389 A1 | 1/2010 | Ogunbona et al. | |
| 2012/0158717 A1 | 6/2012 | Unay et al. | |
| 2012/0242817 A1 | 9/2012 | Pan | |
| 2015/0324469 A1* | 11/2015 | Keyngnaert | G06F 16/9535 707/706 |
| 2017/0344808 A1 | 11/2017 | El-Khamy et al. | |
| 2018/0122065 A1* | 5/2018 | Abedini | G06K 9/4642 |
| 2018/0293460 A1* | 10/2018 | Windmark | G06K 9/621 |

OTHER PUBLICATIONS

C. Szegedy et al., Going Deeper with Convolutions, arXiv:1409.4842 [cs.CV] (Sep. 2014).
C. Szegedy et al., Rethinking the Inception Architecture for Computer Vision, arXiv:1512.00567 [cs.CV] (Dec. 2015).
C. Szegedy et al., Inception-v4, Inception-ResNet and the Impact of Residual Connections on Learning, arXiv:1602.0761 [cs.CV] (Feb. 2016).
The International Search Report (ISR) with Written Opinion for PCT/US2018/025054 dated Dec. 4, 2018, pp. 1-21.
Caicedo, Juan C. et al. "Combining visual 1-18 features and text data for medical image retrieval using latent semantic kernels" Proceedings of the International Conference on Multimedia Information Retrieval (Mar. 29, 2010), pp. 359-366.
Yang, Liu et al. "A Boosting Framework for Visuality-Preserving Distance Metric Learning and Its Application to Medical Image Retrieval" IEEE Transactions on Pattern Analysis and Machine Intelligence, IEEE Computer Society (2010) vol. 32(1), pp. 38-44.
Andre, B. et al "Learning Semantic andVisual Similarity for Endomicroscopy Video Retrieval" IEEE Transactions on Medical Imaging (2012) vol. 31(6), pp. 1276-1288.

* cited by examiner

Mock of the SMILY panel (right) in the pathology frontend along with the classification predictions (left).

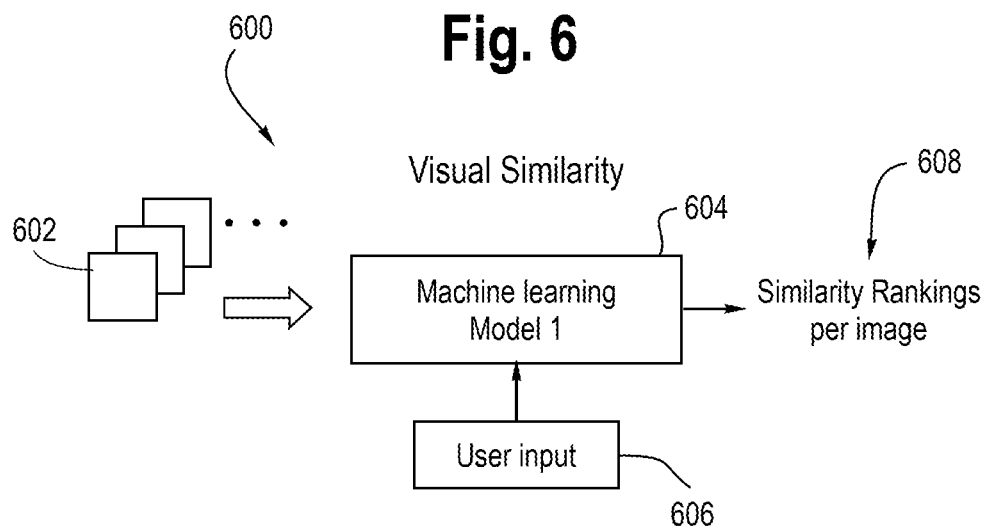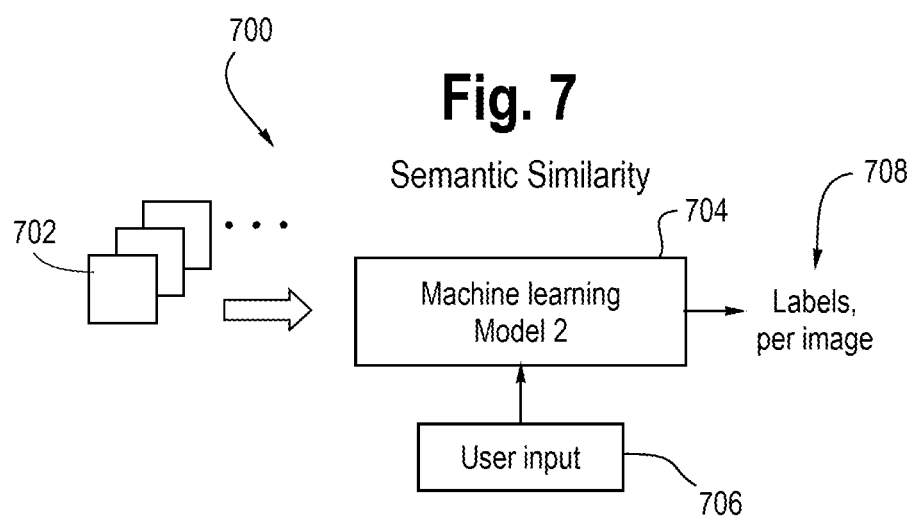

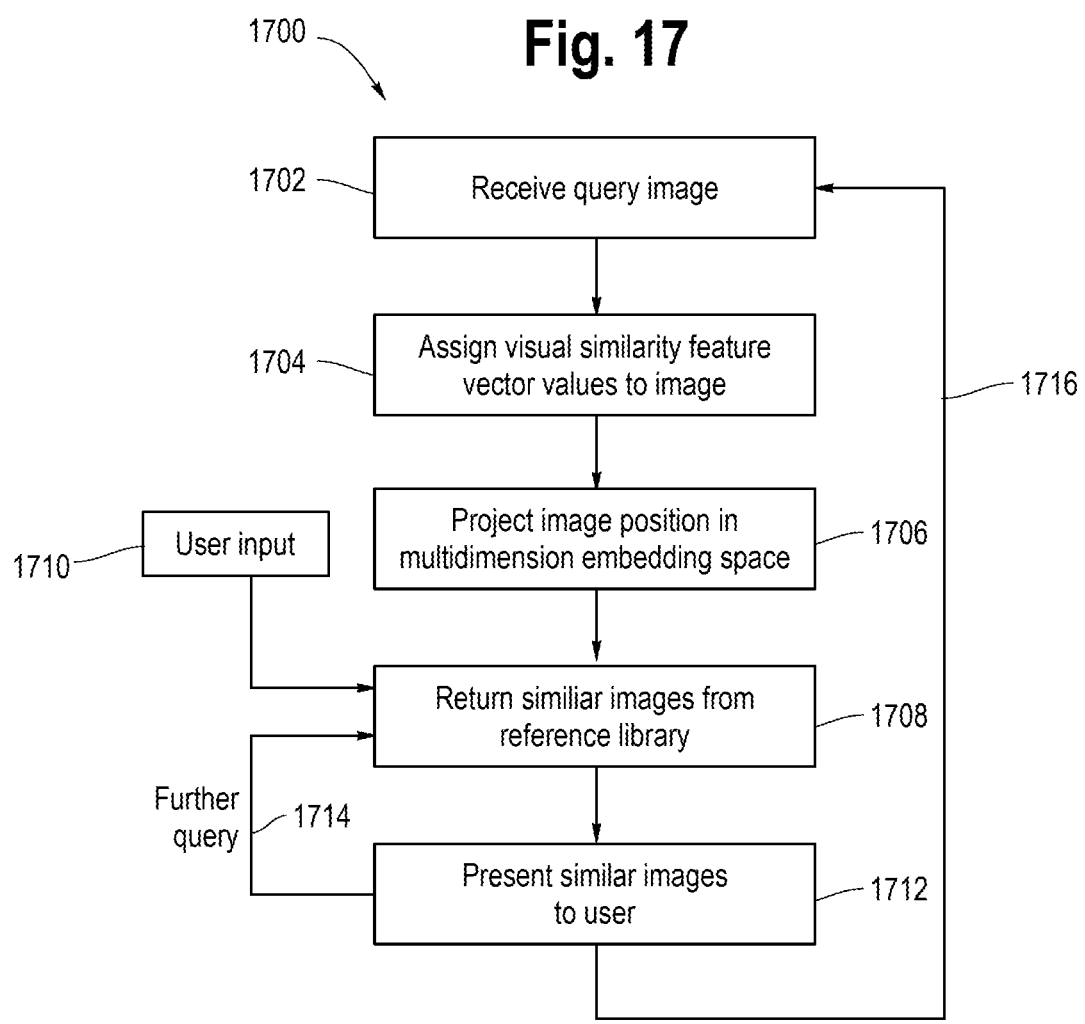

SIMILAR MEDICAL IMAGE SEARCH

BACKGROUND

This disclosure relates to the fields of image searching and retrieval and more particularly to a system and method for searching for similar medical images to an input or query image.

Tools for searching for medical images include commercially available products or services including ARRS Goldminer®, Google's Image Search function, PathoPic, and the Pathology Education Informational Resource (PEIR) Digital Library. PathoPic is a public access image database providing images of high quality for use in medical education and public health information. Some of these tools offer text-based queries for pathology images. There is a body of literature directed to machine learning methods for searching for similar images. See for example J. Wang, et al., Learning fine-grained image similarity with deep ranking, https://arxiv.org/abs/1404.4661 (2017), and the literature cited therein. See also U.S. Pat. Nos. 9,275,456, 9,081,822, 8,199,994, 7,188,103, and 7,027,633, and US patent publications 2012/0242817, 2010/0017389, 2007/0258630, and 2003/0013951.

SUMMARY

In a first aspect, a system is described for searching for similar medical images. The system includes a computer memory system storing a reference library in the form of a multitude of medical images. At least some of the images, and preferably all of them, are associated with metadata including clinical information relating to the specimen or patient associated with the medical images. The system further includes a computer system configured as a search tool for receiving an input image query from a user. The computer system is trained to find one or more similar medical images in the memory system which are similar to the input image. The reference library is represented as an embedding of each of the medical images projected in a feature space having a plurality of axes, wherein the embedding of the medical images is characterized by two aspects of a similarity ranking: (1) visual similarity, and (2) semantic similarity, such that neighboring images in the feature space are visually similar and semantic information is represented by the axes of the feature space. The computer system supports additional queries from a user to thereby further refine a search for medical images similar to the input image within a search space consisting of the one or more similar medical images.

In one embodiment, wherein the medical images are selected from the group of images consisting of retinal images, tissue images, photographs of skin lesions, mammograms, and radiological images.

The system can include a machine learning model or combination of models which assigning visual similarity and semantic similarity feature vectors to the images in the reference library.

The system will ordinarily be used in conjunction with a workstation having a user interface by which a user (e.g., pathologist) selects images, or portions of images as input query images and the workstation provides the input query image to the computer system. In one embodiment, the user interface includes a feature for display of metadata for a selected image in the one or more similar medical image. For example, the display may include the type of tissue, the source of the image, survival data, patient smoker status, etc.

When the similar images are retrieved by the computer system and presented on the workstation, the display of the similar medical images may include a display of a similarity ranking for the similar medical images, such as for example "96% similarity", "52% similarity" etc. This similarity ranking could be obtained for example by the proximity of the projection of the input query image into the embedding and the neighboring images, for example the radius or distance r between the projection and the neighboring images.

The similar medical images could be presented on the workstation in a grouping by case label assigned to the similar medical images, such as "benign", "cancerous", "adenocarcinoma", "Gleason grade 4", etc. The case labels could be determined from metadata associated with the similar medical images or from the axis or axes of semantic similarity along which the similar medical images were found. Alternatively, the similar medical images could be displayed in a ranked list or a pivot table.

In one embodiment the workstation includes a tool for filtering the similar medical images according to user-specified filter criteria, e.g., by smoker status, age, Gleason grade, etc. Such filtering could be performed by reference to the metadata associated with the images.

In one embodiment the further refinement of a search for medical images similar to the input image takes the form of an interactive adjustment of a similarity metric based on user input. The use input could be text input, e.g., by specifying a refinement of a similarity metric such as "broad" or narrow (or radius r in the embedding feature space) or it could be voice input. In the case of voice input, the workstation may include a microphone and speech to text conversion software which converts voice commands into search input parameters.

In one possible configuration, the user interface provides for display of aggregate information about the similar medical images. For example, the aggregate information could take the form of the frequency of diagnostic keywords among the similar medical images, e.g., percent benign, percent cancerous, percent Gleason Grade 3, Gleason Grade 4. As another example the aggregate information could take the form of survival data, such as percent with survival less than two years, and so on.

In still one further configuration, the display of the similar medical images further comprises a summary of results for one or more of the similar medical images including one or more of diagnosis, management; source of image, and survival data. The term "management" means information as to how the patient associated with the image was treated or their disease managed, such as (a) what was done next (after the biopsy or image capture) such as monitoring (+follow up time), (b) prescriptions given (+drug name), (c) additional testing performed (+test name), (d) other treatments performed (+procedure name), and so on.

In another aspect, a method of retrieving similar medical images to an input query image is described. The method includes the step of creating a reference library in the form of a multitude of digital medical images, each of which is associated with image metadata. The digital medical images are supplied to one or more machine learning models and represented as an embedding in the form of a projection of the digital medical images in a feature space having a plurality of axes. The embedding is characterized by two aspects of a similarity ranking: (1) visual similarity, and (2) semantic similarity, such that neighboring images in the feature space are visually similar and semantic information is represented by the axes of the feature space. Similar medical images are retrieved for an input query image within a radius r within the feature space based on a projection of the input query image into the feature space.

In one embodiment of the method, there is a step of refining the retrieval of similar medical images in response to user input. In one embodiment, the user input takes the form of voice input. For example, a user may be using workstation for searching for similar images which includes a microphone and speech to text conversion software which converts voice commands into search input parameters.

In the method, the digital medical images could be retinal images, tissue images, photographs of skin lesions, mammograms, or radiological images such as X-rays or MRI images.

Another aspect of this disclosure is a system for facilitating searching within a medical image, a feature referred to as intra-image searching. In this aspect, the system includes a computer system configured as a search tool for receiving an input query from a user in the form of a portion of a portion of a larger medical image, the computer system including a machine learning pattern recognizer trained to find one or more additional portions of the larger medical image which is similar to the input query. Such pattern recognizers could take several forms and could for example be configured in accordance with one of the following references, the content of which is incorporated by reference herein: C. Szegedy et al., Going Deeper with Convolutions, arXiv:1409.4842 [cs.CV] (September 2014); C. Szegedy et al., Rethinking the Inception Architecture for Computer Vision, arXiv:1512.00567 [cs.CV] (December 2015); see also US patent application of C. Szegedy et al., "Processing Images Using Deep Neural Networks", Ser. No. 14/839,452 filed Aug. 28, 2015. A fourth generation, known as Inception-v4 is considered as another possible architecture for such pattern recognizers. See C. Szegedy et al., Inception-v4, Inception-ResNet and the Impact of Residual Connections on Learning, arXiv:1602.0761 [cs.CV] (February 2016). See also US patent application of C. Vanhoucke, "Image Classification Neural Networks", Ser. No. 15/395,530 filed Dec. 30, 2016, and PCT application serial no. PCT/US2017/019051 filed Feb. 23, 2017.

The system includes a module configured to perform at least one of the following operations on the additional portions of the larger medical image that it found:

a) highlight the additional portions, e.g., by shading in a particular color or showing a bounding box or border around the additional portion;

b) provide annotations for the additional portions, such as probability cancerous or having a particular Gleason score; or c) providing quantifications for the additional portions, such as size data.

The system further includes a workstation for providing a user interface for entering the input query and display of both the input query and the one or more additional portions found by the computer system along with the results of the module performing at least one of the operations.

In this aspect, the medical image could take the form of a retinal image, a tissue image, a photograph of a skin lesions, a mammogram, or a radiological images.

The user interface may also include a feature for display of a similarity ranking for the one or more additional portions to the input query. The one or more additional portions in a ranked list or a pivot table. The user interface could include a tool for filtering the one or more additional portions according to user-specified filter criteria. The user interface supports a further refinement of the search for one or more similar portions based on user input. The user input could be a voice input.

BRIEF DESCRIPTION OF THE DRAWINGS

In FIG. 1, there are results shown for different models that selected similar images from a reference library.

FIG. 6 is an illustration of a process of generating visual similarity rankings for images in the reference library.

FIG. 7 is an illustration of a process of generating semantic labels for images in the reference library.

FIG. 17 is a flow chart showing a series of process steps by which one or more similar images in the reference library are retrieved using the system of FIG. 8.

DETAILED DESCRIPTION

Overview

Figure 1:
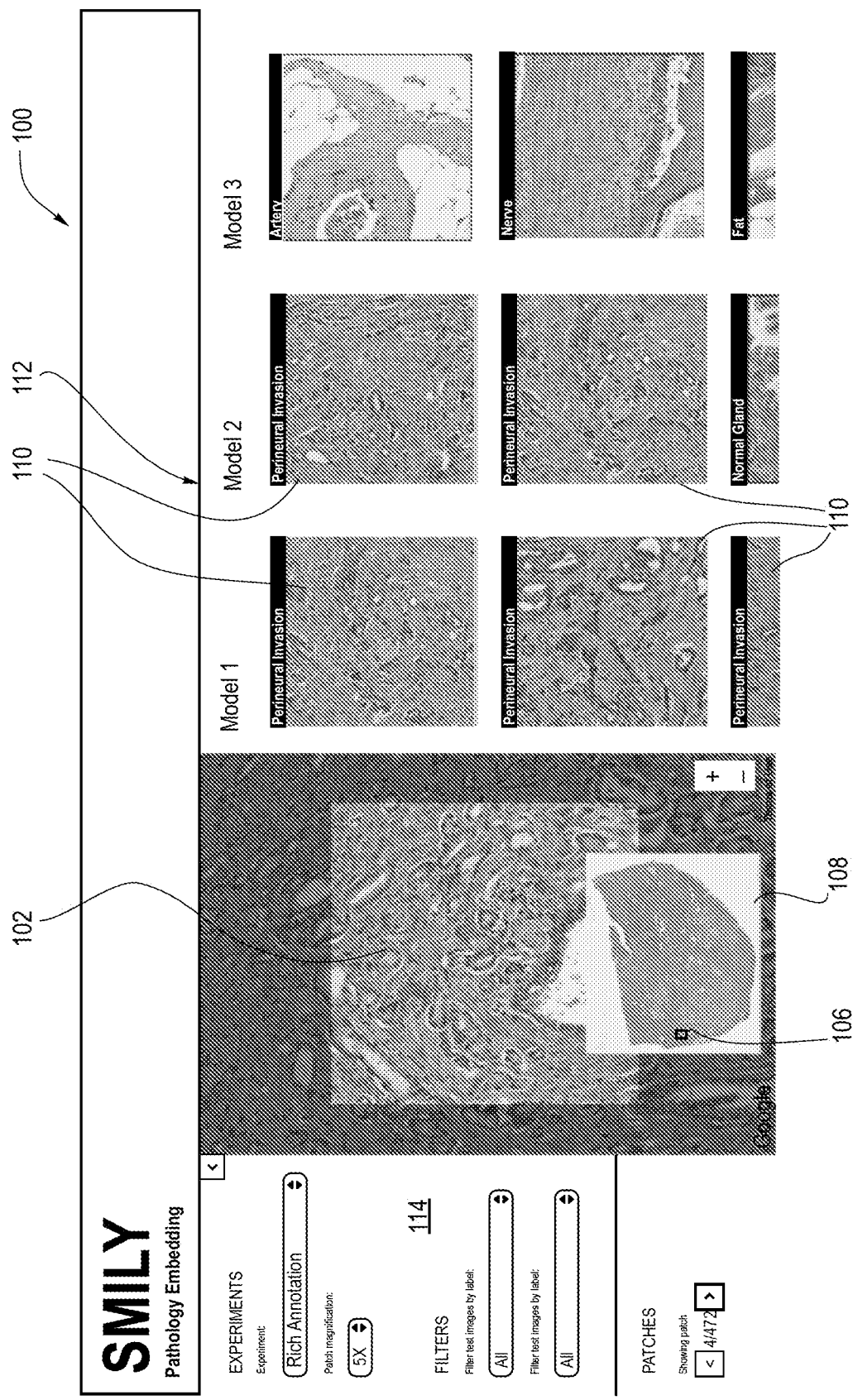
FIG. 1 is an illustration of a display on a workstation showing an input or query image and a set of similar images to the query image in a results pane or pivot table.

This disclosure relates to a system and method for content-based retrieval of medical images which are similar to an input image. The retrieved images are typically presented to a user, such as physician or pathologist, on a workstation display along with metadata associated with retrieved images. The type of medical images for which the system and method can be used can vary depending on the application, but for example could consist of magnified digital images of tissue samples, which are commonly used in the diagnosis of diseases such as cancer. Other applications include images used in radiology, such as chest X-rays and mammograms, and images used in dermatology, such as photographs used in assessment of skin disorders such as skin cancer, dermatitis, microbial skin conditions and chronic skin conditions such as acne or vitiligo.

The system and methods of this disclosure have several applications:
1) Aid in diagnosis—e.g. for a rare tumor, show historic cases of similar morphology that can guide the diagnosis based on (a) comparison to other images as visual reference, and for (b) seeing the metadata of those images. A second example of an application of aid in diagnosis is differential diagnosis—i.e., the visual similar images would be used to distinguish diagnosis A from similar diagnoses B or C. The images would be useful because they (1) show the variability in the population of diagnosis A, but also (2) the different populations of diagnoses B and C in direct comparison to A.
2) Teaching and Education—to see the variability in a population of, e.g. cancerous prostate glands.
3) Label lookup—the metadata served with the similar images can be used to learn the name of a morphological feature, e.g. "nerve" (content-based query).

Additionally, in one further aspect of this disclosure, there is described a method for finding similar features in the same image. For example, in a histopathological gigapixel image, a pathologist may outline a particular region of interest, for example a cluster of cells suspected of being cancerous, and similar regions can be identified and then outlined automatically. This technique serves several useful purposes for the pathologist: it enables quantification over the entire image (e.g. total tumor volume in the slide image); it facilitates creating segmentation annotations; and further it simply facilitates a visual highlighting of all the relevant areas of the specimen that the pathologist might be interested in, and helping to insure that areas the pathologist might have overlooked are not missed.

The system and method of this disclosure can be configured as a user interface set of features, such as screen displays, prompts, windows and user input (query) boxes and retrieval panes or pivot tables, which can be considered as a whole to constitute a clinical decision support tool. In one possible embodiment, the tool does not provide for diagnosis or classification of a queried image per se; rather, it serves images or patches of images that are similar to the queried image to assist a human operator (pathologist) in making medical decisions such as diagnosis, treatment, or estimating prognosis. In an alternative configuration the tool includes generation of a classification label and a probability that the classification label for the query image is correct.

The method has applications in pathology, in particular (a) inter-case searching, namely finding similar image regions in other (historic) cases for aiding in diagnosis, teaching and education, and (b) finding similar features in the same image, e.g., histopathological gigapixel images, such as whole slide images in pathology, as explained above. When viewing a medical image for inter-case searching, the methodology allows for showing the user other images in the same modality that are similar, along with metadata from the other similar images, e.g., the diagnosis, treatment, outcome or other relevant information. Examples of the other relevant information include the distribution (e.g. a histogram, or percentages) of cases across which the queried features occurs (e.g. "30% in benign cases, 20% in cancer grade 1 cases, 45% in cancer grade 2 cases, and 5% in some other rare cancer case").

In our approach we use an embedding of the medical images in the reference library by projecting the medical images into a multidimensional feature space. There are several ways in which this could be accomplished, such as by using unsupervised learning which clusters the images based on similarity of features. As another example we could create embeddings using features learned, for example, in a cancer detection convolutional neural network.

In one aspect, the reference library of stored medical images is represented as an embedding consisting of feature vectors which are projected into a multidimensional space. The feature vectors encode two parts of a similarity ranking: (1) visual similarity, and (2) semantic similarity, i.e., closeness of semantic relationships are represented. We describe several possible machine learning methods for generating visual similarity feature vectors. The embedding can be represented in a multidimensional feature space wherein images having close similarity rankings are grouped near each other. For example, the embedding can be characterized in many dimensions or axes of semantic information, such as tissue type, specimen type, histological features, disease state, etc., and visual similarity indicates the position of the elements of the reference library along such axes, with images having similar visual similarity being clustered close to each other while images that are not visually similar are not clustered close to each other.

Semantic labels refers to semantic information associated with the images, such as "prostate tissue" "breast tissue" "melanoma", "tumor, "benign", "healthy", and so forth, which may be obtained from metadata about a case. Images having the same semantic label are considered semantically similar. Images can be similar in one dimension, e.g., by tissue type label, but different in another dimension, e.g., by tumor type. The generation of semantic similarity labels for medical images can be curated manually or generated from crowdsourced training based on a pathologist click behavior when viewing collections of medical images or other machine learning technique. Another option is to use unsupervised learning to create semantic similarity labels. In one possibility, one would not even use those labels to train a model, but rather as an implementation in a product to retrieve similar images. Semantic labels obtained from metadata allows for assigning images into their respective metadata class (e.g., benign, stage 2, bronchiole, etc.) and similar classes for non-pathology labels such as in dermatology. The similarity ranking, in contrast, is able to provide "proximity" in the embedding space that allows for sorting of images even within the same class.

The use of the embedding approach to searching for medical images enables certain features to be realized, including meaningful similarity metrics, and assessing similarity across multiple dimensions or axes of semantic similarity. Additionally, the methodology supports additional text or voice queries within a given set of search results for a query image. For example, the method may provide for tools for refining search parameters in a second level of searching including using text input (e.g., searching images of patients who are a "smoker," have Gleason Grade 3, patients older than 65, location of lesion, family history, etc.), and retrieving similar images that are filtered in accordance with the text search input. A user may also provide voice input to guide the initial search, such as by speaking "broad" or "narrow" or "smoker" to tailor the search results to suit their particular needs. Such spoken terms "broad", "narrow" or the like allows the user to modulate the algorithms used in the searching, e.g., the size of the sphere in the multidimensional feature space enclosing similar images.

As noted above, in one possible configuration the methods of this disclosure take the form of a clinical decision support tool which is operated by user interface controls on a conventional pathology workstation having a display. Referring now to FIG. 1, there is shown a portion of a display 100 of a workstation in which the user has selected a query image 102. In this example, the query image 102 is a portion 106 (indicated by the small rectangle) of a whole slide image 108 of a tissue sample, e.g., breast or prostate tissue. The tissue sample is stained with a stain such as hematoxylin and eosin (H&E) as is conventional in the art and placed on a microscope slide. A RGB digital image of the slide is obtained from scanning the slide with a whole slide scanner, as is known in the art. The user has selected the image 102 by selecting the slide image 108 from a drop-down menu of available slides for searching (not shown) and navigating and zooming to the point where a particular region of interest in the slide is present in the viewer, indicated by the rectangular query image 102. The query image 102 is then uploaded to a computer system (see FIG. 8) implementing the similar image search feature of this disclosure and the computer system returns a set of similar medical images 110 in a pivot table 112. In this particular example, the computer system implements different machine learning models to return different sets of similar images, each set from a particular model being displayed in a column. The interface includes various tools 114 shown in the left hand side of the display 100 where the user can select different filtering parameters or magnification levels for the query image. For example, the user has selected 5X for the magnification level of the query image 102 and similar image results are returned at 5× magnification and shown in the pivot table 112.

Figure 2:
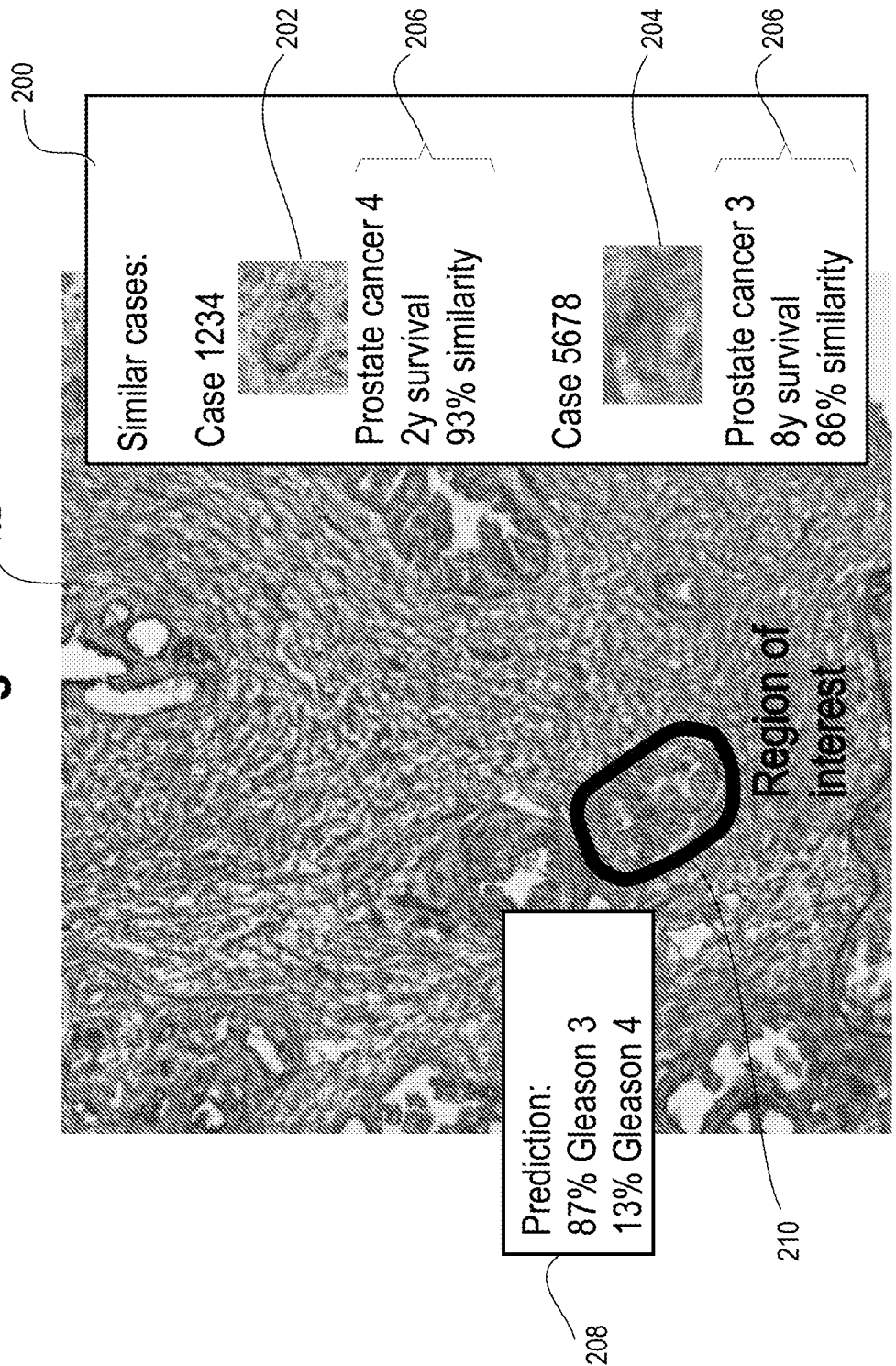
FIG. 2 is an illustration of a query image in the form of a magnified digital image of a prostate tissue specimen and a results pane showing two similar medical images found in the reference library, along with metadata associated with the similar images and classification predictions for the query image.

FIG. 2 is an illustration of a query image 102 in the form of a magnified digital image of a prostate tissue specimen and a results pane 200 showing two similar medical images 202 and 204 found in the reference library, along with metadata 206 associated with the similar images. In this particular example, the computer system implementing the similar medical image search generates classification predictions for the query image, shown at 208, along with confidence levels associated with the predictions. In this case, the computer system includes a pattern recognizer (e.g., deep convolutional neural network) trained to recognized cancerous regions in prostate tissue images and generates a region of interest boundary 210 around a cluster of cells that were predicted to be cancerous, and with a predicted confidence level of a Gleason score for the cancer cells within the boundary based on the similar images found in the search.

Figure 3:
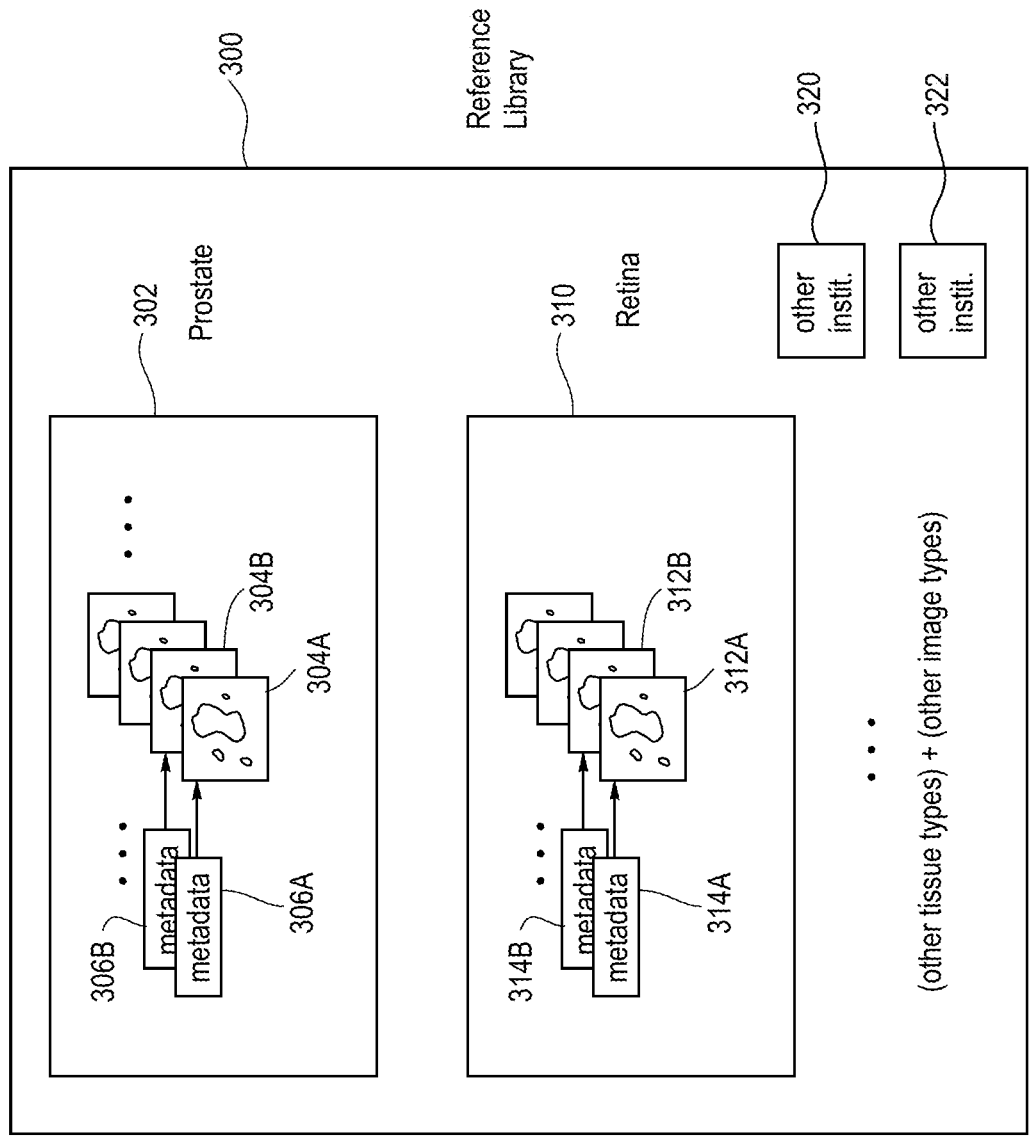
FIG. 3 is an illustration of a reference library consisting of a multitude of medical images of various tissue types and image types. The reference library could be obtained from open sources, licensed from institutions such as universities or hospital systems, or a combination thereof.

As noted above, the search for similar images takes place within a specific universe or collection of images. This collection of images is referred to herein as a "reference library." FIG. 3 is an illustration of a reference library consisting of a multitude of medical images of various tissue types and image types. The reference library could be obtained from open sources, licensed from institutions such as universities or hospital systems, or a combination thereof. For example, in FIG. 3, there is a collection 302 of digital magnified tissue images of prostate tissue samples 304A, 304B, etc., each of which is associated with metadata 306A, 306B, etc. The metadata typically includes some clinical, demographic, survival or other information about the patient providing the sample or the sample itself, such as the patient age, patient smoker status, patient survival data, tissue type, cancer/non-cancer, staining details, etc. In practice, the collection of prostate images will number in the thousands or tens of thousands, or possibly even more. Similarly, a collection 310 of digital fundus (retina) images 312A, 312B . . . and associated metadata 314A, 314B is present in the reference library. The size and content of the reference library may vary depending on the particular implementation and goals of the system providing the searching of this disclosure. In one possible example, the reference library includes similar collections of a variety of different tissue types, including breast, prostate, lung, brain, cervix, and other types of magnified tissue images, as well as radiological images (e.g., mammograms, chest X-rays) and photographic images of skin conditions (e.g., rashes, benign and malignant tumors, dermatitis, etc.). Such images are also preferably accompanied by metadata as is the case of the prostate and retina image collections 302 and 310. The reference library, in whole or in part, could be generated from open sources such as The Cancer Genome Atlas, California Tumor Tissue Registry, etc., or from particular medical institutions 320 and 322 such as hospitals or universities, the U.S. Government or department thereof, such as the Centers For Disease Control, National Institutes of Health, the U.S. Navy, or combinations thereof.

Figure 4:
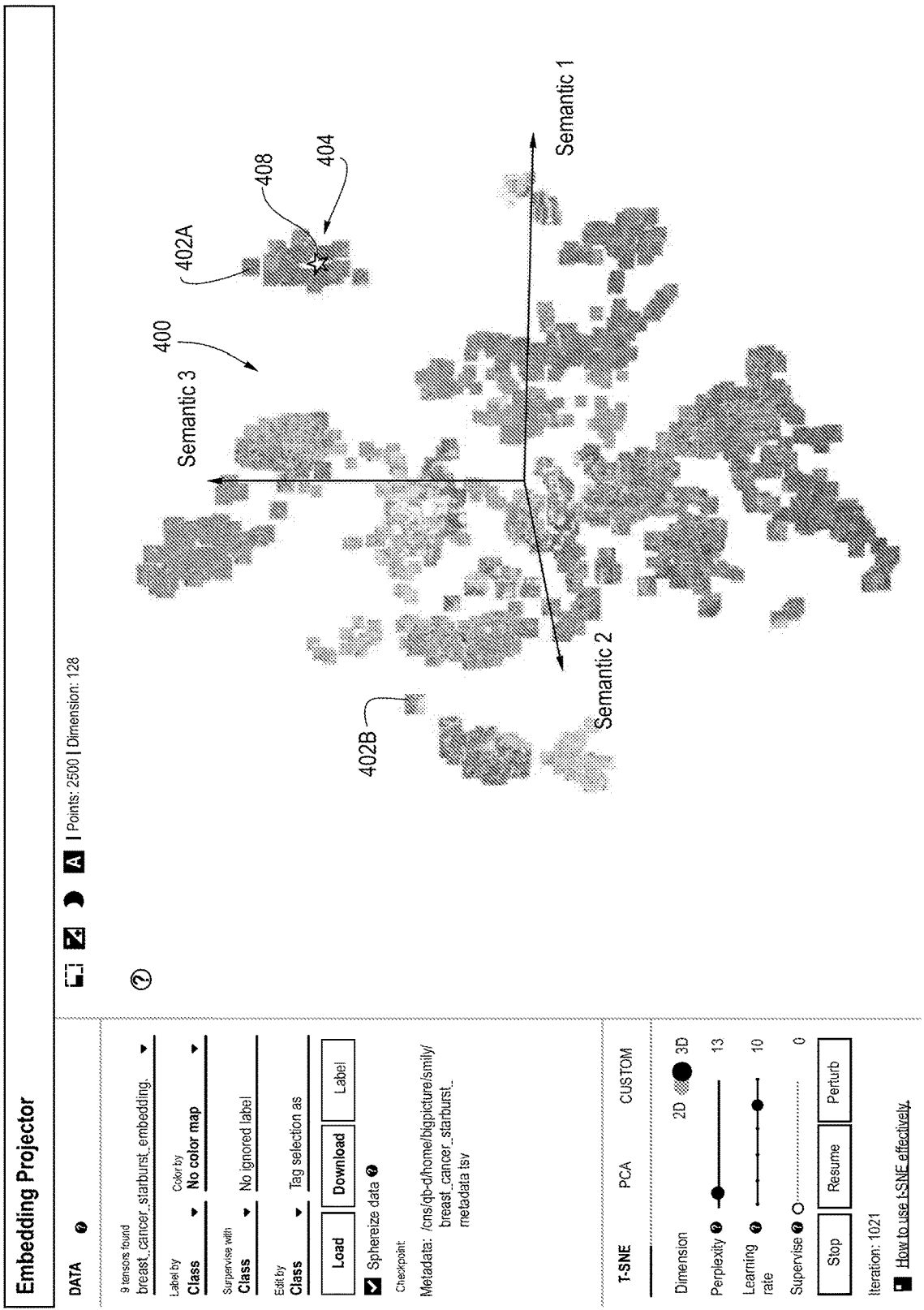
FIG. 4 is an example of a plot of an embedding of multitude of medical images of the reference library of FIG. 3 in a multidimensional space. Each rectangular patch represents a single image in the reference. The position of the images in the embedding is a factor of similarity rankings consisting of visual similarity and semantic similarity. Similar medical images to a query image are found by projecting the query image feature vectors into the embedding and selecting neighboring images.

As explained above, in our system we represent the images in the reference library of FIG. 3 and in particular similarity information between images in the library as a projection of feature vectors of visual similarity and semantic similarity assigned to each image in a multidimensional feature space which we refer to as an embedding. The manner of generating these feature vectors is explained in detail below. FIG. 4 is an example of a plot of an embedding of multitude of medical images of the reference library of FIG. 3 in a multidimensional space or embedding. For sake of ease of visualization of the embedding, the embedding consists of three axes. The axes represent semantic information in the form of a label assigned to the images, for example the axis "semantic 1" is tissue type, the axis "semantic 2" is cancerous, and the axis semantic 3 is smoker status=smoker. Each rectangular patch 402, 402B, etc. represents a single image in the reference library. The position of the images in the embedding is a factor of similarity rankings consisting of visual similarity between the images and semantic similarity. Images that are similar visually are clustered close to each other whereas dissimilar images are not. Similar medical images to a query image are found by projecting the query image feature vectors into the embedding of FIG. 4 and selecting neighboring images, e.g., by designating a sphere of radius r and retrieving, those images within radius r of the projection of the query image in the embedding. For example, referring to FIG. 4, the cluster of images 404 containing image 402A represents a group of images of breast tissue positive for cancer, with smoker status=smoker, and the clustering of the images in the cluster 404 indicates that they have similar visual similarity metric. In this example, if the query image was a breast cancer tissue which happened to contain cancer cells and the patient was a smoker, the query image would be positioned in the location of the star 408 and depending on the radius r some or all of the images in the cluster 402A would be returned.

Figure 5:
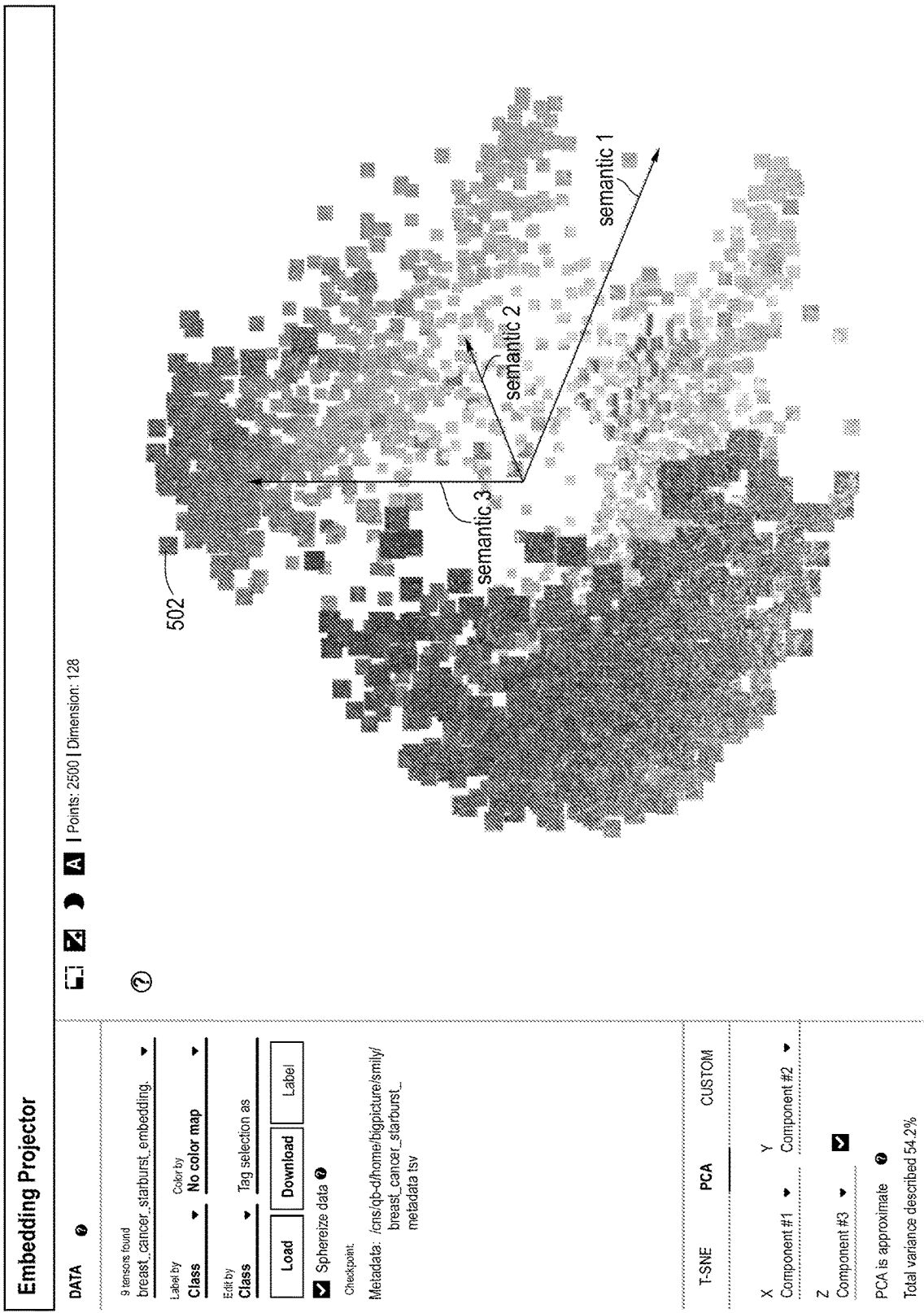
FIG. 5 is another example of a plot of an embedding of multitude of medical images of the reference library of FIG. 3 in a multidimensional space.

FIG. 5 is another example of a plot of an embedding of multitude of medical images of the reference library of FIG. 3 in a multidimensional space. Semantic 1, semantic 2 and semantic 3 refer to axes of the space, and the meaning thereof can be specified by a user or operator if they wish to see a visualization of the images in the reference library. The individual rectangles 502 represent the images in the reference library. The rectangles 502 can be color coded so as to group together related images to make the plot of the embedding more intelligible or useful to the user. For example, images of a given smoker status of "not smoker" could be colored green, for example where none of the axes semantic 1, semantic 2 and semantic 3, are associated with smoker status but instead to other labels assigned to the images.

FIG. 6 is an illustration of a process of generating visual similarity rankings for images in the reference library of FIG. 3. In essence, the images 602 are supplied to a machine learning model 604 ("machine learning model 1") which generates similarity rankings 608 per image. The machine learning model may also use user input 606 in generating the similarity rankings, depending on the machine learning approach and whether it is supervised, or uses crowdsourced input. FIG. 7 shows a method for generating semantic labels which are used for similarity ranking among images in the reference library. The images 702 are fed to a second machine learning model 704, e.g., a deep convolutional neural network pattern recognizer which generates semantic labels for the images, such as healthy, benign, or assigns a tissue type label.

A variety of possible deep learning methods may be used for the machine learning model 1 of FIG. 6 and in a preferred embodiment a machine learning model or combination of models assigns both the visual similarity and semantic similarity feature vectors to the image in one process or procedure, eliminating the need for performing a separate step of using a second model to assign semantic similarity.

In one possible example, activation layers of trained convolutional neural networks may produce similarity rankings between the images 602.

In another example, the model 604 may be implemented in accordance with the techniques described in the paper of J. Wang, et al., Learning fine-grained image similarity with deep ranking, https://arxiv.org/abs/1404.4661 (2017), the content of which is incorporated by reference herein. The use of this methodology may require some consideration of how large of an image to feed into the model of the Wang et al. paper. This consideration is related to what desired scale for morphological similarity. For example, in some contexts, such as with gigapixel tissue images, one may want to do the visual similarity on a patch-by-patch basis and not the entire image. Improved performance of the model may be achieved when using a square patch centered on a cell and including, on average, all of the cell plus some of the neighbor cells. This may make particular sense when the phenotypes pathologists care about are single rather than multi-cell. Depending on the tissue type and disease, one may likely have a priori belief about what the relevant scales would be. The appropriate weighting for each scale could be handled by simple concatenation of the embedding or potentially by a learned network operating on top of the model represented by the Wang et al. paper if some ground-truth training samples are available.

Other examples for the machine learning model 604 include unsupervised learning techniques, autoencoders and self-supervised approaches, including context encoders, see https://people.eecs.berkeley.edu/~pathak/context_encoder/ and unsupervised visual representation learning by context prediction, see http://graphics.cs.cmu.edu/projects/deepContext/.

A combination of these approaches may also be used. For instance, semantic features from the Wang et al. method might be able to distinguish between different histological features, whereas activation layers from a tissue specimen classifier as additional embedding might help to differentiate specimen type (e.g. prostate vs breast vs breast tissue), and a diagnostic classifier (e.g. tumor detector, prostate Gleason score classifier, mortality risk predictor) might help to further distinguish between risk categories with the same tissue type. At a high level, the Wang et al. method works by using human labeled triplets: a human is shown two reference images, A and B, and then they are asked to rate whether a third image C is more similar to A or to B. Repeat that for many thousands of triplets, and you get a similarity ranking for images A, B and C—that is the similarity metric that defines how the images A, B and C are projected in the multidimensional space of FIGS. 4 and 5. This method can be crowdsourced or spread across many different users (e.g., pathologists) during a model training exercise. The embedding consists of feature vectors that have two parts of similarity ranking: 1) visual similarity (based on the triplet ranking above) and 2) semantic similarity—which was trained on labels assigned to the images initially and the user's click behavior, e.g., during crowdsourcing of distributed training. E.g., if a user in the training exercise searched for "prostate tissue", clicked on the image of prostate tissue, the image is associated with that label. Images with the same label, e.g., prostate tissue, are then considered to be semantically similar.

It will be noted that the images in the reference library are preferably associated with metadata, which may indicate things such as tissue type. The metadata would only allow for assigning images into the respective metadata class (e.g. tumor, benign, stage 2, bronchiole, etc, and similar for non-pathology labels such as in dermatology). The similarity ranking, in contrast, is able to provide "proximity" in the embedding space that allows for sorting images even within the same class. Insofar as the semantic aspect of the similarity ranking, it could help to subgroup according to features within the same class (e.g. glands more elongated or more spherical, within the same tumor type).

Figure 8:
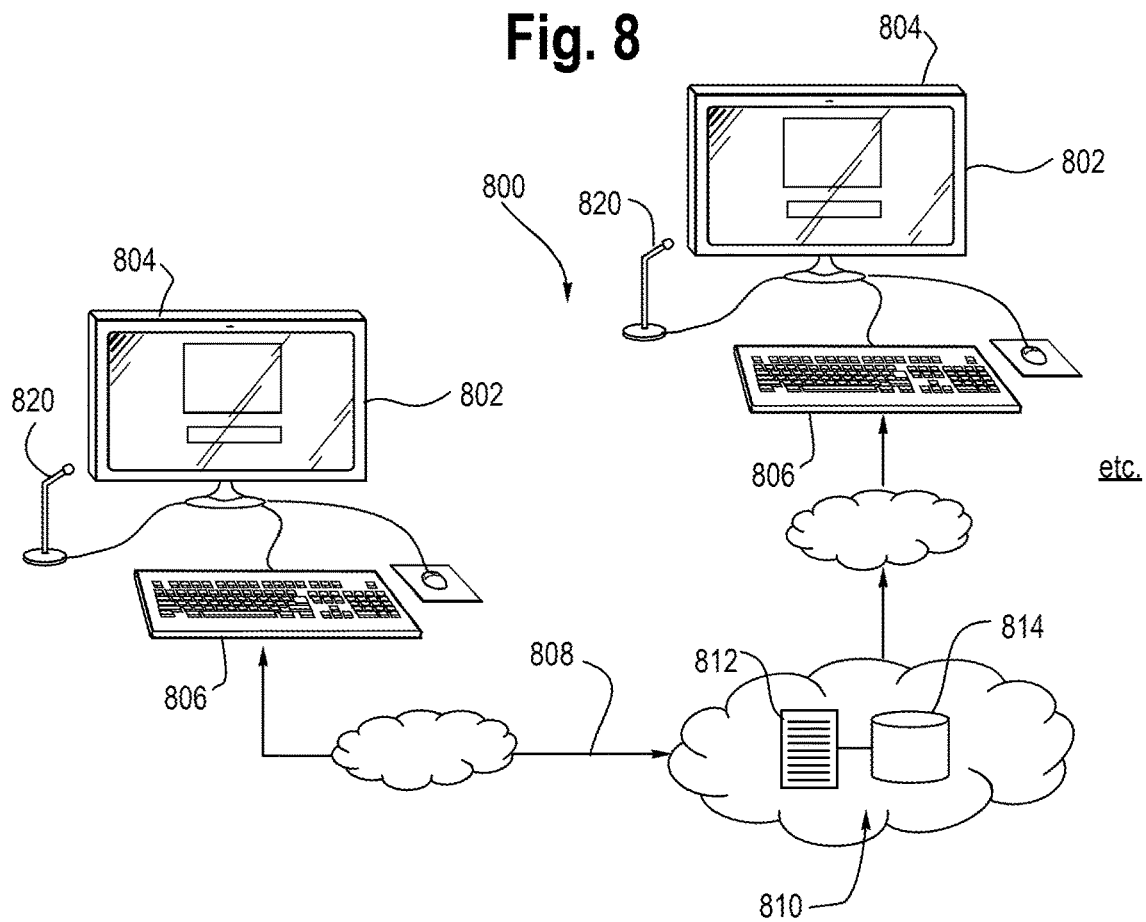
FIG. 8 is an illustration of a computing system environment in which the methods of this disclosure are practiced in one possible implementation.

FIG. 8 is an illustration of a computing system environment 800 in which the methods of this disclosure are practiced in one possible implementation. A workstation 802 includes a display 804 and user interface devices 806 such as keyboard and mouse to browse through collections of images, typically stored locally, and selects an image for which they would like to search for similar images. The selected image is then uploaded over a network 808 to a computer system 810 including a image server 804 and a data store 812 containing the reference library. The computer system 810 stores data representing the embedding of the images in the reference library in a multidimensional feature space (FIGS. 4 and 5) and then using the machine learning model of FIGS. 6 and 7 (or combination thereof), also implemented in the computer system 810, generates visual and semantic feature vectors for the query image and projects those vectors into the embedding. Depending on the parameters of the search (e.g., narrow or broad) and hence the radius in the embedding space, nearby images in the space representing similar images are returned to the workstation. The process is conducted in real time for multitude of workstations 804, e.g., in a distributed embodiment where the provider of the computer system 810 services multiple institutions or users of the similar medical image search service. The workstations may optionally include a microphone 820 which allows the user to enter voice commands to the workstation. The workstation includes a speech recognition engine that converts the speech to text and permit voice control over search parameters. For example, the user can speak the phrase "broad search", and data indicating a search with a large value for r in the embedding space is desired. The computer system interprets this command when retrieving similar images such that the workstation receives a larger collection of similar images than it otherwise would have. Similarly, the spoken command "narrow" may tailor the search to small values of r in the embedding space such that only a limited set of similar images are returned, namely only the images that have the highest visual and semantic similarity rankings to the query image.

Figure 9:
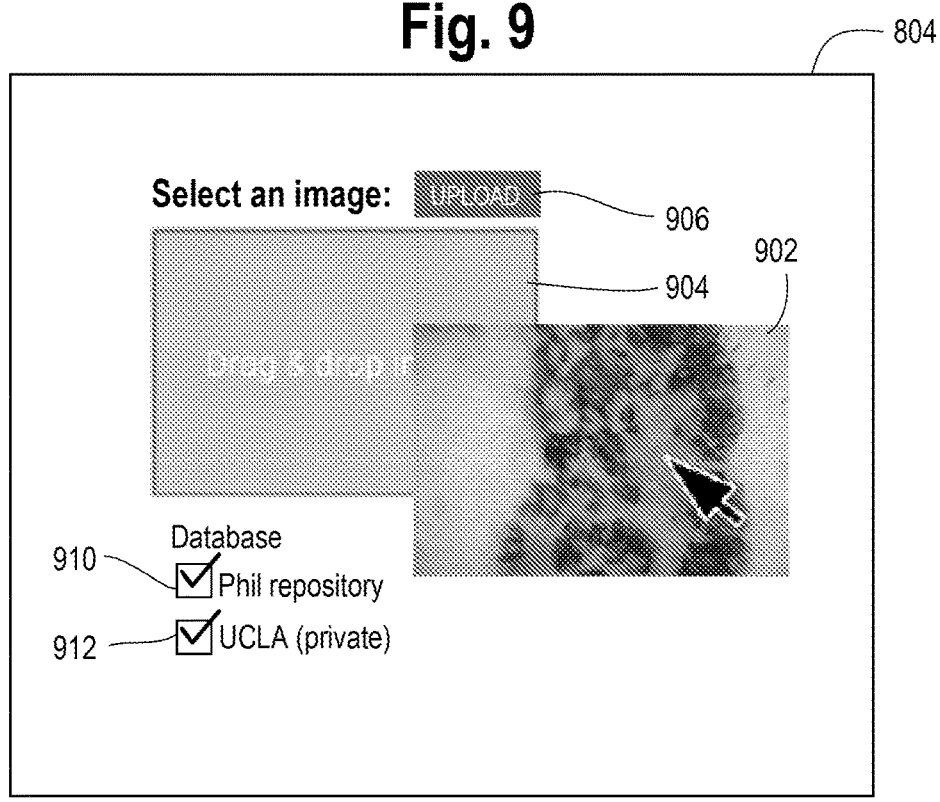
FIG. 9 is an illustration of a display on a workstation showing the user selecting a query image via a drag and drop technique. The same procedure of drag and drop could be performed for a part of an image, for example in pathology where a user defines a bounding box or square around some tissue region and then they drag and drop that bounding box or square.

FIG. 9 is an illustration of a display on a workstation showing the user selecting a query image for use in the method. In this example, the user selects a query image 902 from a menu of available images (not shown), the image 902 appears on the display and is dragged and dropped into a box 904. The user selects the upload icon 906. The user is given a choice of databases to search in, by checking the box 910, 912 next the name of the institution or source of the images in the reference library. The same procedure of drag and drop could be performed for a part of an image, for example in pathology where a user defines a bounding box or square around some tissue region (e.g., by a series of mouse clicks which create a boundary around the region of interest) and then they drag and drop that bounding box or square into a box 904 and then select the upload icon. As another alternative, the menu of available images could be either a selection of whole images (e.g., in dermatology photographs of skin lesions), or a selection of regions of interest which are just portions of an overall image, e.g., in the context of tissue pathology.

Figure 10:
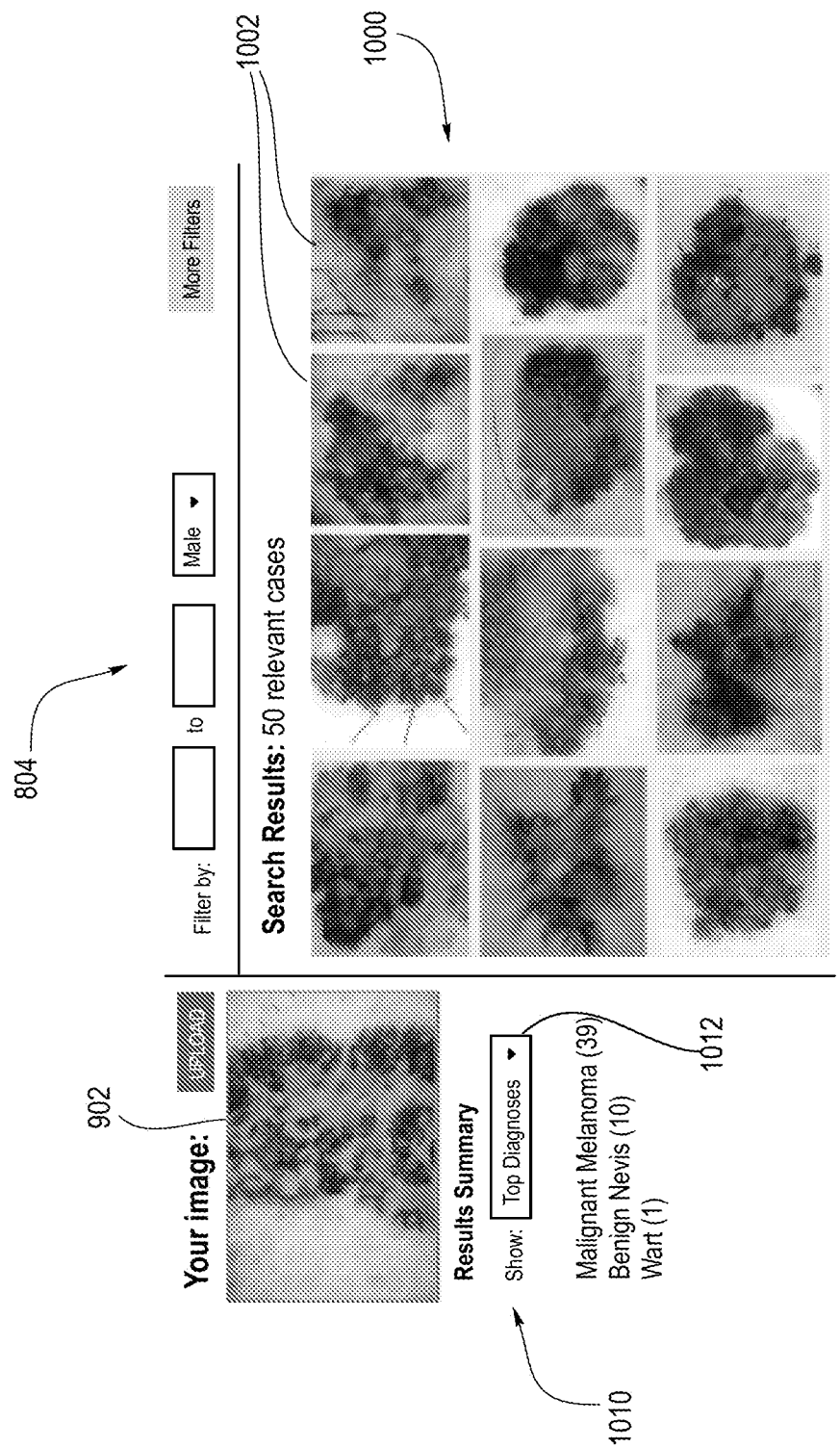
FIG. 10 is an illustration of a display on a workstation showing a query image and a pivot table showing a portion of fifty different similar medical images retrieved from the reference library.

FIG. 10 is an illustration of a display on a workstation showing a query image 902 and a pivot table 1000 showing a portion of fifty different similar medical images 1002 retrieved from the reference library. The task bar 1004 provides tools for filtering the retrieved images, e.g., on the basis of metadata associated with each of the images. For example, the user could select filters such that only images of cancerous lesions are displayed, only images from male or female patients, only images with a survival time of less than 5 years, etc. In the results region 1010, the user is given an option to show statistics of the returned images, such as the top diagnoses for all 50 images returned, which are listed in the region 1010. A drop-down box 1012 allow for the user to select other statistics or summaries of the returned images. The menu of options available in the drop-down box will vary on the type of images and persons skilled in the art will be able to arrive at a suitable menu of options depending on implementation details which are not particularly important. Examples of such options include Diagnosis; Management, e.g. what was done next such as Monitoring (+follow up time), Rx (+drug name), Additional Testing (+test name), Other Treatment (+procedure name); and Sources (which university/organization supplied this data)

Figure 11:
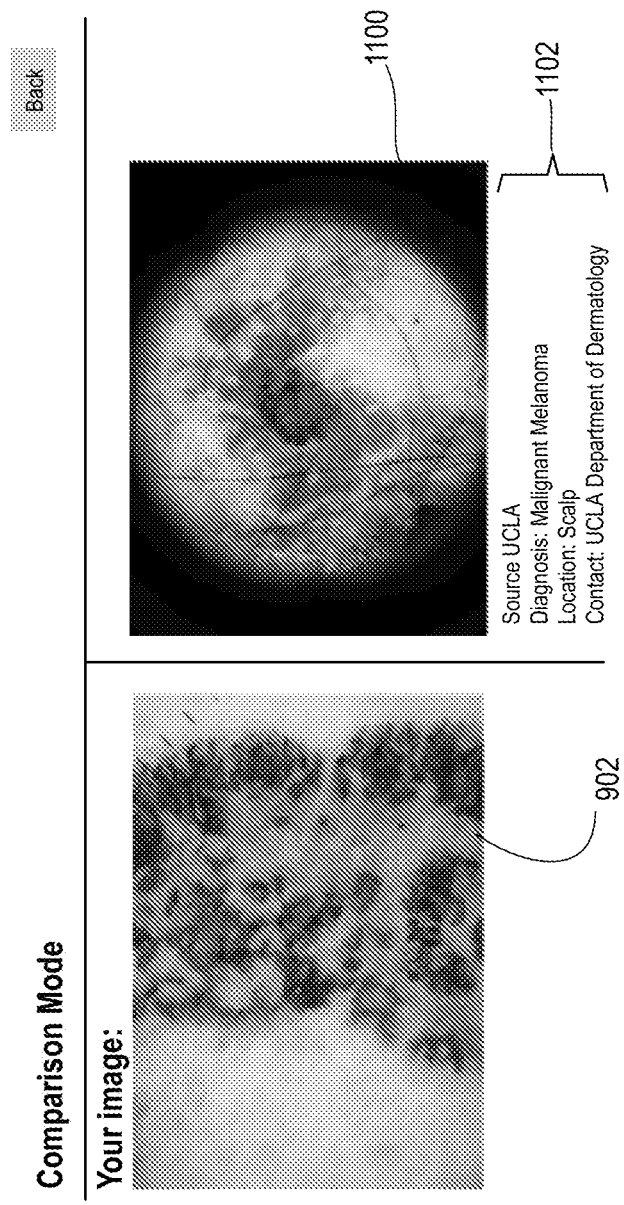
FIG. 11 is an illustration of a display on a workstation showing a query image and an image from the reference library in a comparison mode.

FIG. 11 is an illustration of a display on a workstation showing, a query image 902 and a similar image 1100 from the reference library in a comparison mode. For example, the user selects one of the images from FIG. 10 and the display enters the comparison mode shown in FIG. 11. The similar image 1100 in this example is a photograph of a lesion appearing on the scalp and associated with a diagnosis of melanoma. The information from the metadata of the image 1100 is presented in the field 1102 below the image.

Figure 12:
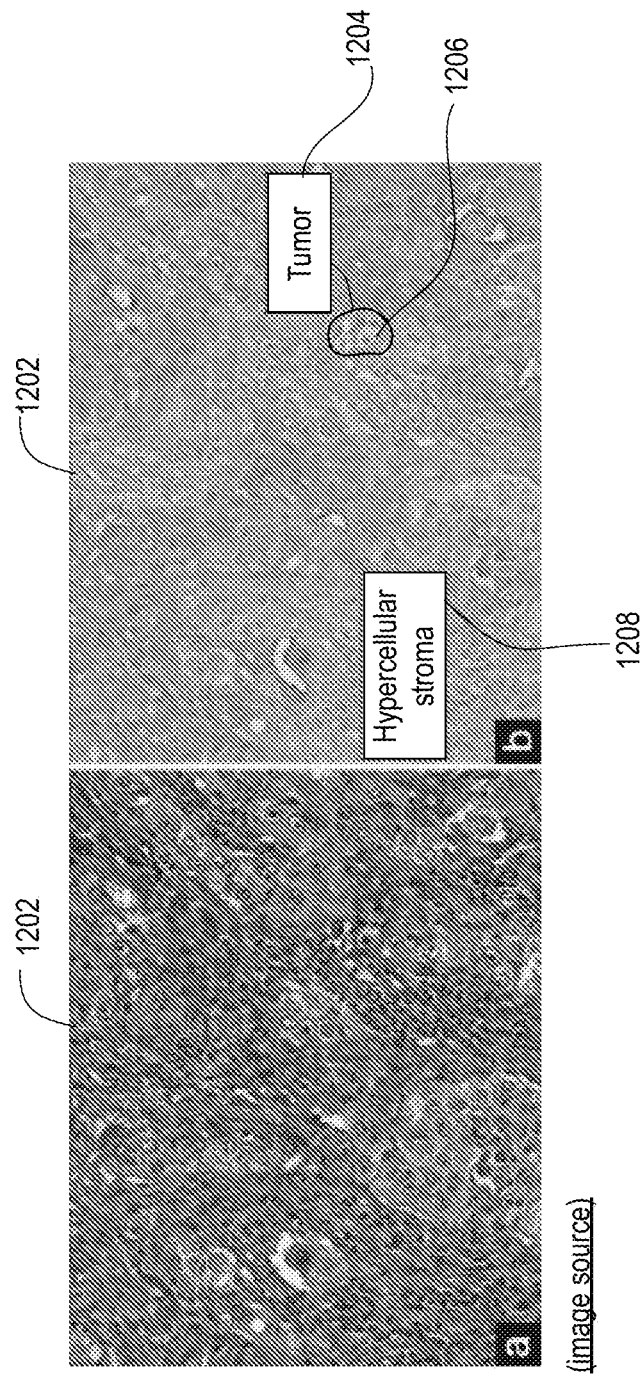
FIG. 12 is an illustration of a display on a workstation showing a query image and the query image with automatic detection of regions of interest such a tumor cells in the query image.

FIG. 12 an illustration of a display on a workstation showing a query image 1202. The machine learning model in the computer system 810 of FIG. 8 implements a convolutional neural network pattern recognizer which is trained to identify tumor cells in magnified tissue images of the type of the query image. When similar images are returned, in one possible embodiment the query image is also returned with automatic detection of regions of interest such as tumors in the query image. For example the query image 1202 is augmented with a label "tumor" 1204 and a mask or border 1206 surrounding a cluster of cells which were identified by the pattern recognizer as containing cancer cells. The pattern recognizer identifies peripheral cells as "hypercellular stroma" and returns a label 1108 and color codes such areas of the query image.

Figure 13:
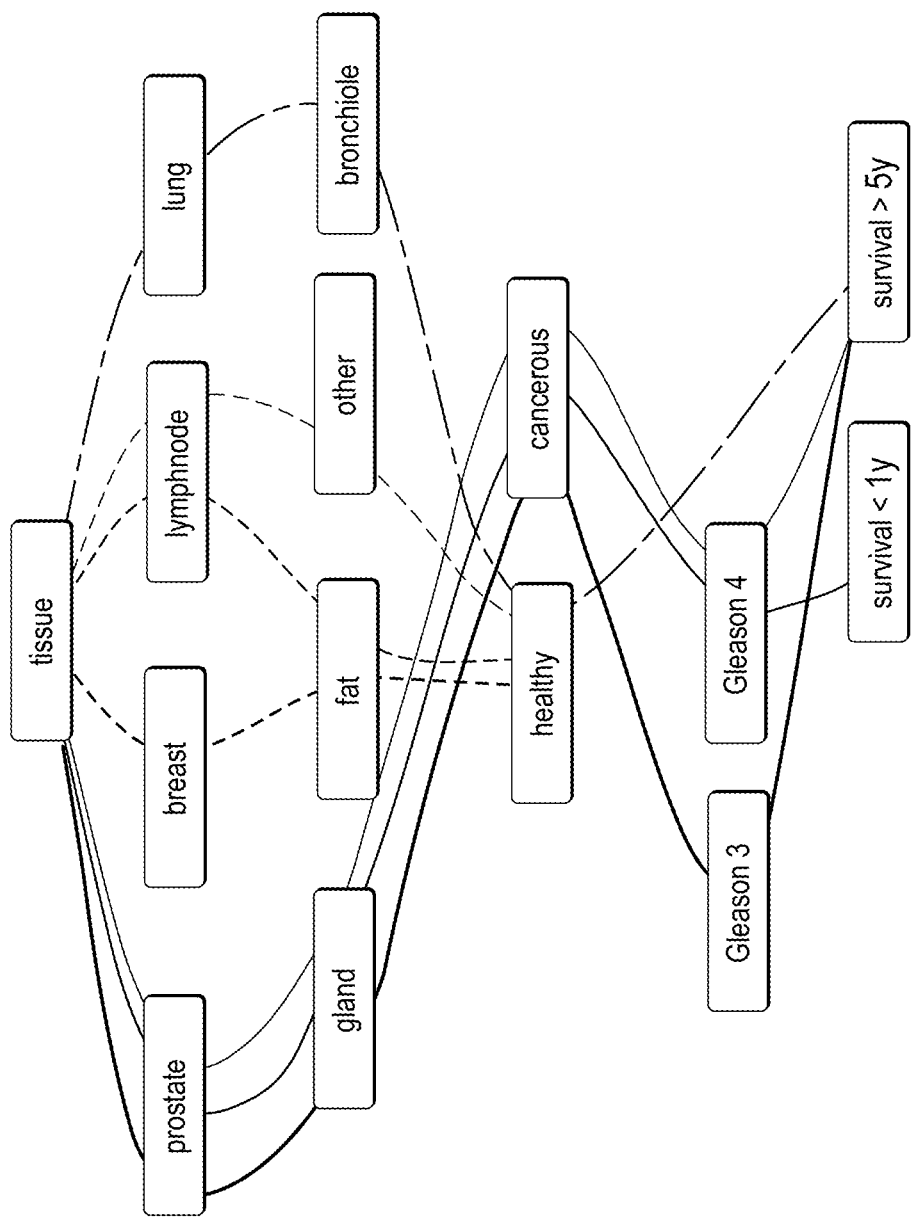
FIG. 13 is a similarity graph showing one possible hierarchy for determining semantic similarity.
Figure 14:
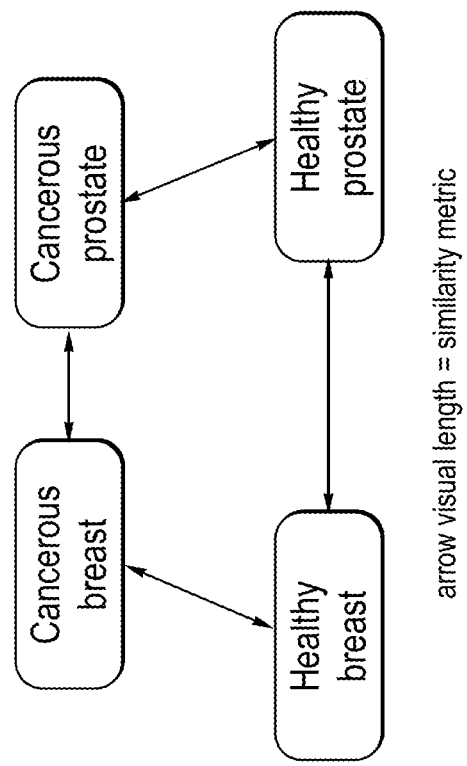
FIG. 14 an graph showing degrees of visual similarity between cancerous and healthy breast and prostate tissue.

The clinical decision support tool of this disclosure is intended to identify "similar" image patches, where, in contrast to natural images of cats and dogs, the definition of "similar" is not a priori clear. In one embodiment, the objective is to provide a tool that serves images and cases that are useful for the pathologist/user in the context of the current image. As such, the tool should capture basic histology to discriminate specimen types, histological features (e.g. glands, bronchioles, epithelial tissue, fat tissue) and within those categories then ideally also discriminate between different tumor severities (e.g. a prostate gland with Gleason 4 vs Gleason 5 cancer). One can take a variety of different approaches in defining or determining "similarity." FIG. 13 is a similarity graph showing one possible hierarchy for determining semantic similarity. The graph shows sample paths through a similarity graph. Tissue images with similar paths should be considered similar. Note that the hierarchy in this graph is not necessarily the only or best hierarchy for similarity. For instance, "cancerous breast tissue" might in some cases be regarded to be more similar to "cancerous prostate tissue" than to "healthy breast". Further, the finer grained distinctions (e.g. Gleason 3 vs Gleason 4) could be important for the usefulness of the tool to make actual diagnosis, e.g. for finding historic rare cases with a similar tumor. FIG. 14 is a graph showing degrees of visual similarity between cancerous and healthy breast and prostate tissue. The length of the arrows indicates a visual similarity metric, that is the shorter the arrow the closer they are visually. Cancerous tissue of different organs might be more similar to the respective healthy tissue because cancerous tissue is morphologically less differentiated, in particular with increasing tumor grade.

Figure 15:
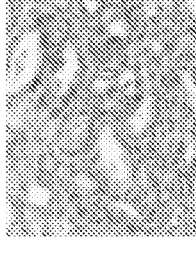
FIG. 15 is a plot of different dimensions of semantic similarity. The dimensions shown in FIG. 15 (tissue type, specimen type, histological features, and disease) may be represented as different coordinate axes in the multidimensional feature space of FIGS. 4 and 5.

The considerations of FIGS. 13 and 14 can be considered internal concepts for dimensions of similarity (similar to FIG. 15), and different applications could emphasize different ones. FIG. 13 specifically presents a coarse example for a possible hierarchy in what the similarity search should be able to distinguish. One example to visualize this would be a hierarchical clustering of all images, and where the nodes in the graph of FIG. 13 correspond to clusters of images. Going down in the hierarchy corresponds to finer-grained distinctions in the cluster hierarchy. FIG. 14 illustrates the concepts of different dimensions (e.g. benign vs cancer, or prostate tissue vs breast tissue) in yet another way FIG. 15 is a plot of different dimensions of semantic similarity. The dimensions shown in FIG. 15 (tissue type, specimen type, histological features, and disease) may be represented as different coordinate axes in the multidimensional feature space of FIGS. 4 and 5. For example, within the dimension of tissue, there are different types of tissues in magnified tissue images, such as stroma, blood vessel and fat tissue. Specimen type dimension includes different types of organs, such as kidney, breast, cervix, prostate, etc. Histological features dimension includes gland (prostate), gland (breast), and bronchiole (lung). Disease dimension includes for example different degrees or Gleason scores of prostate adenocarcinoma. In the space of FIGS. 4 and 5, each location of each point on a given dimension would give rise to the respective association—where applicable (e.g. there might be an axis of how much the glands are deformed or fused, and the degree of which that is the case might result in different cancer stages).

Figure 16:
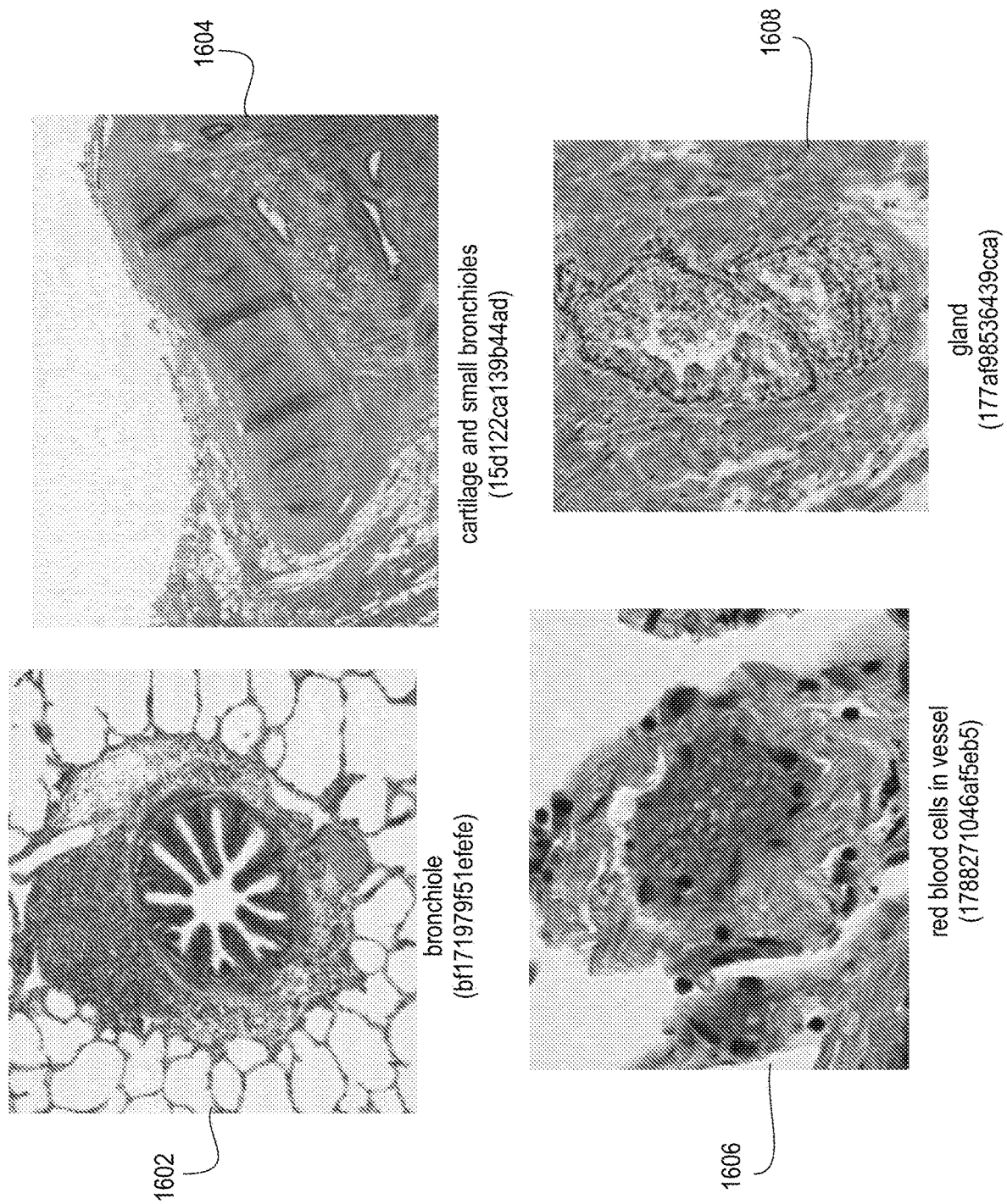
FIG. 16 is an illustration of images of four different types of anatomical features which are examples of the types of images for which the present method is useful for retrieving similar images.

FIG. 16 is an illustration of images of four different types of anatomical features which are examples of the types of images for which the present method is useful for retrieving similar images. These include bronchiole features 1602, cartilage and small bronchioles 1604, red blood cells in blood vessels 1606, and glands 1608.

One of the key challenges for pathology in general is the question of how to define "similarity". In one approach, images could be considered as similar if viewing them (and their corresponding case data such as diagnosis, treatment, outcome) will help a pathologist to make an accurate diagnosis for the case at hand. Generally this would mean that both diagnostic as well local anatomical features should be similar, but defining the ground truth for these is not straightforward and will likely have to be a combination of multiple features:
1. Diagnostic classification (e.g. tumor classifier network features)
2. Organ from which the tissue was extracted
3. Visual features
4. Histological features (e.g. prostatic alveoli, ducts, perineural invasion, etc)
5. Similar morphology (e.g. the shape of glands, etc.)
6. Similarity labels assigned to images which are generated by pathologists, e.g., crowdsourced from an implementation of the Wang et al. method.

Another option for looking at similarity may be biological similarity (from small to big) on one axis (numbered below) and degree or type of abnormality along 2nd axis (indicated by letters below):
1. Proteomic (e.g., are these cell both expressing PDL-1?)
   a. Overexpression
   b. Underexpression
2. Cellular (does cell A look like cell B—e.g. is this an activated lymphocyte)
   a. Nuclear & cytoplasmic features (mitotic count)
   b. Differentiation
3. Structural (how are cells organized in relation to each other—eg. glandular breast tissue)
   a. Organization
   b. Invasion (perivascular, perineural, etc)
4. Histological/tissue type (adipose, muscle)
   a. Carcinoma vs sarcoma
   b. Histological grade
5. Organ/specimen type (breast, lung, prostate)
   a. Enlarged
   b. Other These axes could be another possible way to represent the embedding multidimensional space of FIGS. 4 and 5. The placement of the reference library images along the these axes could assigned by machine learning models (see FIGS. 6-7) or by a machine learning method generating the visual similarity and semantic similarity metrics in a single model or combination of models as explained above.

FIG. 17 is a flow chart showing a series of process steps by which one or more similar images in the reference library are retrieved using the computer system 810 of FIG. 8.

At step 1702, a query image is received in the computer system 810.

At step 1704, visual similarity feature vector values are assigned to the query image using the machine learning model 1 of FIG. 5.

At step 1706 the feature vector of visual similarity is projected in the multidimensional embedding space of FIGS. 4 and 5.

At step 1708 similar medical images are returned from the reference library, e.g., by finding images within radius r of the projected query image in the embedding space. User input also may occur in step 1710 such as by specifying the search parameters, filter parameters, or speech input for example indicating broad or narrow search.

At step 1712 the returned images are provided over the network to the workstation and the displayed on the display of the workstation. The user may submit further queries, e.g., to narrow the search results or only return a subset of the images, as indicated by the loop 1714, as which point a new set of images is returned. The process may loop back to the beginning as indicated by loop 1716 and the initiation of a new search for similar images for a new query image. Further queries can also be used to focus the search results along a specific subset that shares a very specific feature (i.e. the initial results could all be somehow similar, but the refined subset could focus on e.g. images that are similar with respect to the nuclei density, or a very unique morphological feature that might only occur in a certain rare cancer type). So the further queries would be a way of user interaction to "tell" the system what kind of similarity the user is interested in.

Another aspect of this disclosure is a system for facilitating searching within a medical image, a feature referred to as intra-image searching. In this aspect, the system includes a computer system configured as a search tool for receiving an input query from a user in the form of a portion of a portion of a larger medical image. The computer system including a machine learning pattern recognizer trained to find one or more additional portions of the larger medical image which is similar to the input query. Such pattern recognizers could take several forms and could for example be configured in accordance with one of the following references, the content of which is incorporated by reference herein: C. Szegedy et al., Going Deeper with Convolutions, arXiv:1409.4842 [cs.CV] (September 2014); C. Szegedy et al., Rethinking the Inception Architecture for Computer Vision, arXiv:1512.00567 [cs.CV] (December 2015); see also US patent application of C. Szegedy et al., "Processing Images Using Deep Neural Networks", Ser. No. 14/839,452 filed Aug. 28, 2015. A fourth generation, known as Inception-v4 is considered as another possible architecture for such pattern recognizers. See C. Szegedy et al., Inception-v4, Inception-ResNet and the Impact of Residual Connections on Learning, arXiv:1602.0761 [cs.CV] (February 2016). See also US patent application of C. Vanhoucke, "Image Classification Neural Networks", Ser. No. 15/395,530 filed Dec. 30, 2016, and PCT application serial no. PCT/US2017/019051 filed Feb. 23, 2017.

The system includes a module configured to perform at least one of the following operations on the additional portions of the larger medical image that it found:

a) highlight the additional portions, e.g., by shading in a particular color or showing a bounding box or border around the additional portion;

b) provide annotations for the additional portions, such as probability cancerous or having a particular Gleason score; or c) providing quantifications for the additional portions, such as size data.

The system further includes a workstation (e.g., FIG. 1) for providing a user interface for entering the input query, e.g., FIG. 9, and display of both the input query and the one or more additional portions found by the computer system along with the results of the module performing at least one of the operations, similar to as shown in FIG. 1.

In this aspect, the medical image could take the form of a retinal image, a tissue image, a photograph of a skin lesions, a mammogram, or a radiological images.

The user interface may also include a feature for display of a similarity ranking for the one or more additional portions to the input query. The one or more additional portions in a ranked list or a pivot table. The user interface could include a tool for filtering the one or more additional portions according to user-specified filter criteria. The user interface supports a further refinement of the search for one or more similar portions based on user input. The user input could be a voice input.

User Interaction

There are several possible user interaction details that may be implemented in the workstation tools or features on the display:

1. Selecting a similar image could show more information for that particular case, and/or show the entire image larger or in a dedicated viewer, or move to that image as the "source" or query image for similar image search.

2. The result set of multiple similar images could be shown simultaneously, e.g. in a ranked list ordered by decreasing similarity, and with diagnosis keywords.

3. The ranked list of similar results could serve to show both the intra-class variability (e.g. different appearances of prostate Gleason 3 cancer), or the (ideally lower) similarity to other classes it can be confused with (e.g. prostate Gleason 4 cancer).

4. The tools on the display could interactively adjust the similarity metric based on the user's input, to facilitate an iterative search. In particular, the result set can be refined based on the previous choices of the user. If, for example, the user selected an image of similar cancer grade (but dissimilar histological features), more images of the similar cancer grade could be shown by emphasizing that particular dimension in the metric embedding space for the neighbor list search.

5. Additional useful output can be provided in the form of aggregate information about the similar images in the neighborhood, e.g. showing diagnostic keywords along with their frequency among the similar images.

6. Group the resulting images by the case label that is known for them, e.g., group by "benign", "adenocarcinoma grade 3", "adenocarcinoma grade 4" etc.

Example Use Cases

The following use cases are framed for dermatology, but can be easily applied toward pathology, ophthalmology, or radiology.

Use Case #1: Double Checking a Diagnosis

Dr. Lee is a general dermatologist who has a patient with a suspicious mole. She has arrived at a diagnosis, but wants to double check her assessment.

1. She (or her medical assistant) takes a picture of the lesion. She selects the image using the user interface tools shown in the previous figures and the tool automatically finds cases similar to the one she just diagnosed.

2. A pivot table (e.g., FIG. 1) is presented of the e.g., 50 cases that were identified as morphologically similar. The table shows the diagnosis & percent of cases with that diagnosis.

3. If most of the identified cases are in line with her assessment, she's reassured that she made the right diagnosis. If most of historical cases fall into another diagnostic category, she can take another look at her current case and compare it to historical cases to make a final diagnosis. There is a differential diagnosis benefit here as well. In particular, Dr. Lee might see images from a quite similar disease B, which however by comparison to disease A help her to decide that the case is really disease A and not B. The similar images would be useful because they (1) show the variability in the population of disease A, but also (2) the different populations of diseases B and C in direct comparison to A.

4. She also wants to be able to browse the cases identified to compare them manually to the current case. Hence, she selects any of the cases in the pivot table and browses the images and reviews associated metadata.

5. She also wants to be able to highlight a region of interest and find cases that match that region (and perhaps not the rest of the slide). Hence, she navigates to a portion of the image containing a region of interest, draws a mask around that region, and using zoom tools centers the region of interest in the viewer. That region is dragged and dropped into the box for indicating the query image to search for similar images. Cases with similar regions of interest are retrieved from the library.

Use Case #2: A Challenging Case

Dr. Lee has a challenging case where the diagnosis is a mystery. She wants to know the likelihood of different diagnoses so that she can figure out what the next step in management should be (refer or not, urgency of referral, empiric treatments she should try). She selects an image of the area of interest, and the system returns a set of say 50 similar images along with metadata of each of the images. The display includes summary data, such as a list of the diagnosis for the images, management strategies, and treatments. The images are shown on the workstation grouped according to diagnosis or disease state.

Use Case 3) Teaching and Education

A student is assigned a task to search for similar images of cancerous prostate glands. The search is specified to be wide, to cover a variety of different Gleason score samples. The student can then see the variability within a population of, e.g., cancerous prostate glands at different Gleason scores, and can filter the results to particular Gleason scores, or filter by age, or smoker status, or other factor.

Use Case 4) Label Lookup

A user investigates a portion of a tissue image for which the user in uncertain of its classification or diagnostic significance. The tissue images is supplied as a query image and the computer system returns a set of 25 different images of the same type of tissue and having similar morphology. The metadata served with the similar images can be used to learn the name of a morphological feature, e.g. "nerve".

Intra-Image Search

Another aspect of this disclosure is a method and system for searching within an image for other similar portions to a portion of an image designated by a user. For example, a user viewing a magnified tissue image may identify a region containing a particular type or class of cells (e.g., tumor cells) and the method searches for other areas in the image for other cells of that type or class.

The system facilitating searching within a medical image includes a computer system configured as a search tool for receiving an input query from a user in the form of a portion of a portion of a larger medical image. The input query could be a portion of the image that is user defined, e.g., by the user drawing a mask or border around the portion. The computer system including a machine learning pattern recognizer trained to find one or more additional portions of the larger medical image which is similar to the input query. For example, the pattern recognizer could be trained to find tumor cells. There is a module in the computer system configured to perform at least one of the following operations on the additional portions of the larger medical image:

a) highlight the additional portions (e.g., by showing a whole slide image with additional tumor cell regions shown in red or some contrasting color);

b) provide annotations for the additional portions (e.g., predicted Gleason score in a prostate tissue sample); or c) providing quantifications for the additional portions (e.g., by providing some size or cell count metrics or other information).

The system further includes a workstation for providing a user interface for entering the input query and display of both the input query and the one or more additional portions found by the computer system along with the results of the module performing at least one of the operations.

In one configuration the medical image is an image selected from the group of images consisting of retinal images, tissue images, photographs of skin lesions, mammograms, and radiological images. The user interface may includes a feature for display of a similarity ranking for the one or more additional portions to the input query. The user interface may display the one or more additional portions in a ranked list, e.g., ranked by similarity to the input query. The user interface can include a tool for filtering the one or more additional portions according to user-specified filter criteria, such as by size, cell count, similarity, Gleason score etc. The user interface can supports a further refinement of the search for one or more similar portions based on user input. For example if the search returns 100 different similar regions the user could filter the search to only find similar portions with the highest similiarity or a particular Gleason score. As another example, the user may wish to specify a broad search and the search results could be expanded to include more similar image portions but with lower similarity metric. The user input could be provided by simple commands on the user interface of the workstation, or could be provided by voice command, in the situation where the workstation has a microphone and speech recognition engine to convert voice commands to text input.

Privacy Considerations

All of the images in the reference library are patient de-identified, and they are patient de-identified when they are returned as search results. Ethics review and institutional review board exemption is obtained from each institution from which the images are obtained. Patient data was not linked to any Google user data. Furthermore, for the reference images our system includes a sandboxing infrastructure that keeps each image dataset separated from each other, in accordance with regulation, data license and/or data use agreements. The data in each sandbox is encrypted; all data access is controlled on an individual level, logged, and audited.

We claim:

1. A system for searching for similar medical images, comprising a computer memory system storing a reference library comprising a multitude of medical images, at least some of which are associated with metadata including clinical information relating to a specimen or a patient associated with the medical images;

a computer system configured as a search tool for receiving an input image query from a user, wherein the computer system is trained to find one or more similar medical images in the memory system which are similar to the input image, wherein reference library is represented as an embedding of each of the medical images projected in a feature space having a plurality of axes, wherein the embedding is characterized by two aspects of a similarity ranking: (1) visual similarity, and (2) semantic similarity such that neighboring images in the feature space are visually similar and semantic information is represented by the axes of the feature space, and wherein the computer system supports additional queries from a user to thereby further refine a search for medical images similar to the input image within a search space consisting of the one or more similar medical images; and a user interface configured to:
display the one or more similar medical images; and
display aggregate information about the one or more similar medical images, wherein the aggregate information comprises frequency of diagnostic keywords among the similar medical images.

2. The system of claim 1, wherein the medical images comprise images selected from the group of images consisting of retinal images, tissue images, photographs of skin lesions, mammograms, and radiological images.

3. The system of claim 1, further comprising a machine learning model or combination of models assigning visual similarity and semantic similarity feature vectors to the images in the reference library.

4. The system of claim 1, wherein the user interface is further configured to display metadata for a selected image in the one or more similar medical images.

5. The system of claim 4, wherein the display of metadata data includes a display of survival data.

6. The system of claim 4, wherein the display of metadata further includes a display of a similarity ranking for the one or more similar medical images.

7. The system of claim 1, wherein the user interface is further configured to show the one or more similar medical images in a grouping by case label assigned to the similar medical images, and wherein the case label is selected from the group of labels consisting of "benign", "cancerous", and "adenocarcinoma".

8. The system of claim 1, wherein the user interface is further configured to display the one or more similar medical images in a ranked list.

9. The system of claim 1, wherein the user interface is further configured to display the one or more similar medical images and a tool for filtering the one or more similar medical images according to user-specified filter criteria.

10. The system of claim 1 wherein the further refinement of a search for medical images similar to the input image comprises interactive adjustment of a similarity metric based on user input.

11. The system of claim 10, wherein the user input comprises a voice input.

12. The system of claim 1, wherein the reference library is obtained from open sources or from medical institutions.

13. The system of claim 1, wherein the user interface is further configured to display a list of reference libraries from which the reference library is selectable.

14. The system of claim 1, wherein the user interface is further configured to display the one or more similar medical images, and wherein the display of the one or more similar medical images further comprises a summary of results for one or more of the similar medical images including one or more of diagnosis, management of disease, source of image, and survival data.

15. A method of retrieving similar medical images to an input query image, comprising the steps of:
- creating a reference library in the form of a multitude of digital medical images, each of which is associated with image metadata;
- supplying the digital medical images to one or more machine learning models and representing the digital medical images as an embedding in the form of a projection of the digital medical images in a feature space having a plurality of axes, wherein the embedding is characterized by two aspects of a similarity ranking: (1) visual similarity, and (2) semantic similarity, such that neighboring images in the feature space are visually similar and semantic information is represented by the axes of the feature space;
- retrieving similar medical images for an input query image within a radius r within the feature space based on a projection of the input query image into the feature space;
- displaying, on a user interface, the similar medical images; and
- displaying, on the user interface, aggregate information about the similar medical images, wherein the aggregate information comprises frequency of diagnostic keywords among the similar medical images.

16. The method of claim 15, further comprising the step of refining the retrieval of similar medical images in response to user input.

17. The method of claim 16, wherein the user input comprises voice input.

18. The method of claim 15, wherein the digital medical images comprise images selected from the group of images consisting of: retinal images, tissue images, photographs of skin lesions, mammograms, and radiological images.

19. A system for facilitating searching within a medical image, comprising:
- a computer system configured as a search tool for receiving an input query from a user in the form of a portion of a larger medical image, the computer system including a machine learning pattern recognizer trained to find one or more additional portions of the larger medical image which is similar to the input query;
- a module in the computer system configured to highlight the additional portions of the larger medical image; and
- a user interface for entering the input query and display of both the input query and the one or more additional portions found by the computer system along with the highlighted additional portions of the larger medical image.

20. The system of claim 19, wherein the medical image comprises an image selected from the group of images consisting of retinal images, tissue images, photographs of skin lesions, mammograms, and radiological images.

* * * * *